United States Patent
Olson (10) Patent No.: US 8,465,465 B2
(45) Date of Patent: Jun. 18, 2013

(54) DYNAMIC, REDUCED-PRESSURE TREATMENT SYSTEMS AND METHODS

(75) Inventor: Jonathan Scott Olson, Houston, TX (US)

(73) Assignee: KCI Licensing, Inc., San Antonio, TX (US)

(*) Notice: Subject to any disclaimer, the term of this patent is extended or adjusted under 35 U.S.C. 154(b) by 773 days.

(21) Appl. No.: 12/621,340

(22) Filed: Nov. 18, 2009

(65) Prior Publication Data

US 2010/0125259 A1 May 20, 2010

Related U.S. Application Data

(60) Provisional application No. 61/116,121, filed on Nov. 19, 2008.

(51) Int. Cl.
*A61M 1/00* (2006.01)

(52) U.S. Cl.
USPC .............................. 604/313; 604/319; 210/640

(58) Field of Classification Search
USPC ...................... 604/313, 319, 540, 543; 602/41
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Melanie Hand (57) ABSTRACT

A dynamic, reduced-pressure treatment system generates reduced pressure and a wave experienced at a tissue site where the wave may have a frequency in the range of from 0.5 Hertz to 20 Hertz. The system includes a manifold for delivering reduced pressure to the tissue site, a sealing member forming a fluid seal over the tissue site, a reduced-pressure source for providing reduced pressure, a reduced-pressure delivery member for delivering reduced pressure from the reduced-pressure source to the manifold, and a wave generator associated with the reduced-pressure delivery member for imparting a wave to the reduced pressure developed by the reduced-pressure source. A reduced-pressure delivery member with liquid-impermeable-and-gas-permeable element may be applied to help reduce blockages and to facilitate ease of treatment. Other systems, apparatuses, and methods are disclosed.

25 Claims, 5 Drawing Sheets

U.S. PATENT DOCUMENTS

| | | |
|---|---|---|
| 3,585,964 A | 6/1971 | Skoldberg |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,398,767 B1 | 6/2002 | Fleischmann |
| 6,488,643 B1 | 12/2002 | Tumey et al. |
| 6,493,568 B1 | 12/2002 | Bell et al. |
| 6,553,998 B2 | 4/2003 | Heaton et al. |
| 6,695,823 B1 | 2/2004 | Lina et al. |
| 6,814,079 B2 | 11/2004 | Heaton et al. |
| 6,994,702 B1 | 2/2006 | Johnson |
| 7,004,915 B2 | 2/2006 | Boynton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143346 A1 | 10/2002 | Tumey |
| 2007/0167927 A1 | 7/2007 | Hunt et al. |
| 2007/0239078 A1* | 10/2007 | Jaeb ............................. 601/2 |
| 2008/0269651 A1* | 10/2008 | Warlick et al. ............... 601/11 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 81 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 93/009727 | 5/1993 |
| WO | WO 94/020041 | 9/1994 |
| WO | WO 96/05873 | 2/1996 |
| WO | WO 97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion date mailed Jul. 5, 2010 for PCT International Application No. PCT/US2009/064993.

* cited by examiner

DYNAMIC, REDUCED-PRESSURE TREATMENT SYSTEMS AND METHODS

RELATED APPLICATION

The present invention claims the benefit, under 35 U.S.C. §119(e), of the filing of U.S. Provisional Patent Application Ser. No. 61/116,121, entitled "Dynamic, Reduced-Pressure Treatment System and Method," filed 19 Nov. 2008, which is incorporated herein by reference for all purposes.

BACKGROUND present invention relates generally to medical treatment systems and, more particularly, to dynamic, reduced-pressure systems and methods.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "NPWT," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue site and channeling fluids that are drawn from the tissue site. The possible benefits of treating a tissue site with reduced pressure include reduction in edema, enhanced blood flow, promotion of granulation of tissue, decreasing of bacterial colonization, removing of inhibiting agents, promotion of a moist healing environment, and enhanced epithelial migration.

SUMMARY

Problems with existing reduced-pressure treatment systems and methods are addressed by the systems and methods of the illustrative, non-limiting embodiments described herein. According to an illustrative, non-limiting embodiment, a dynamic, reduced-pressure treatment system for treating a tissue site on a patient includes a manifold for placing adjacent to the tissue site, a sealing member for coupling to the patient's epidermis to form a fluid seal over the tissue site, a reduced-pressure source for producing reduced pressure, a reduced-pressure delivery member for delivering reduced pressure from the reduced-pressure source to the manifold, and a wave generator associated with the reduced-pressure delivery member. The wave generator imparts a wave to the reduced pressure developed by the reduced-pressure source.

According to another illustrative, non-limiting embodiment, a method for manufacturing a dynamic, reduced-pressure treatment system for treating a tissue site on a patient includes the steps of: providing a manifold for placing adjacent to the tissue site, providing a sealing member for coupling to the patient's epidermis and operable to form a fluid seal over the tissue site, providing a reduced-pressure source for developing a reduced pressure, and providing a reduced-pressure delivery member for delivering reduced pressure from the reduced-pressure source to the manifold. The method further includes the steps of providing a wave generator and associating the wave generator with the reduced-pressure delivery member. The wave generator imparts a wave to the reduced pressure developed by the reduced-pressure source.

According to another illustrative, non-limiting embodiment, a method for treating a tissue site on a patient includes the steps of: disposing a manifold adjacent to the tissue site, placing a sealing member on the patient's epidermis to form a fluid seal over the tissue site, fluidly coupling a reduced-pressure delivery member to the manifold, and fluidly coupling the reduced-pressure delivery member to a reduced-pressure source for providing reduced pressure to the manifold. The method further includes associating a wave generator with the reduced-pressure delivery member. The wave generator imparts a wave to the reduced pressure developed by the reduced-pressure source.

According to another illustrative, non-limiting embodiment, a reduced-pressure delivery member includes a first lumen for transmitting a liquid and a second lumen for transmitting a gas. The first lumen has a first interior space and the second lumen has a second interior space. A first liquid-impermeable-and-gas-permeable member is coupled to the second lumen in at least a portion of the second interior space.

According to another illustrative, non-limiting embodiment, a reduced-pressure delivery member includes a first lumen for transmitting a gas and a second lumen for transmitting a liquid. The first lumen has a first interior space and the second lumen has a second interior space. The first lumen is formed at least in part from a fluid impermeable material. The second lumen is formed from a gas-permeable-and-liquid-impermeable material and is disposed within the first interior space.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
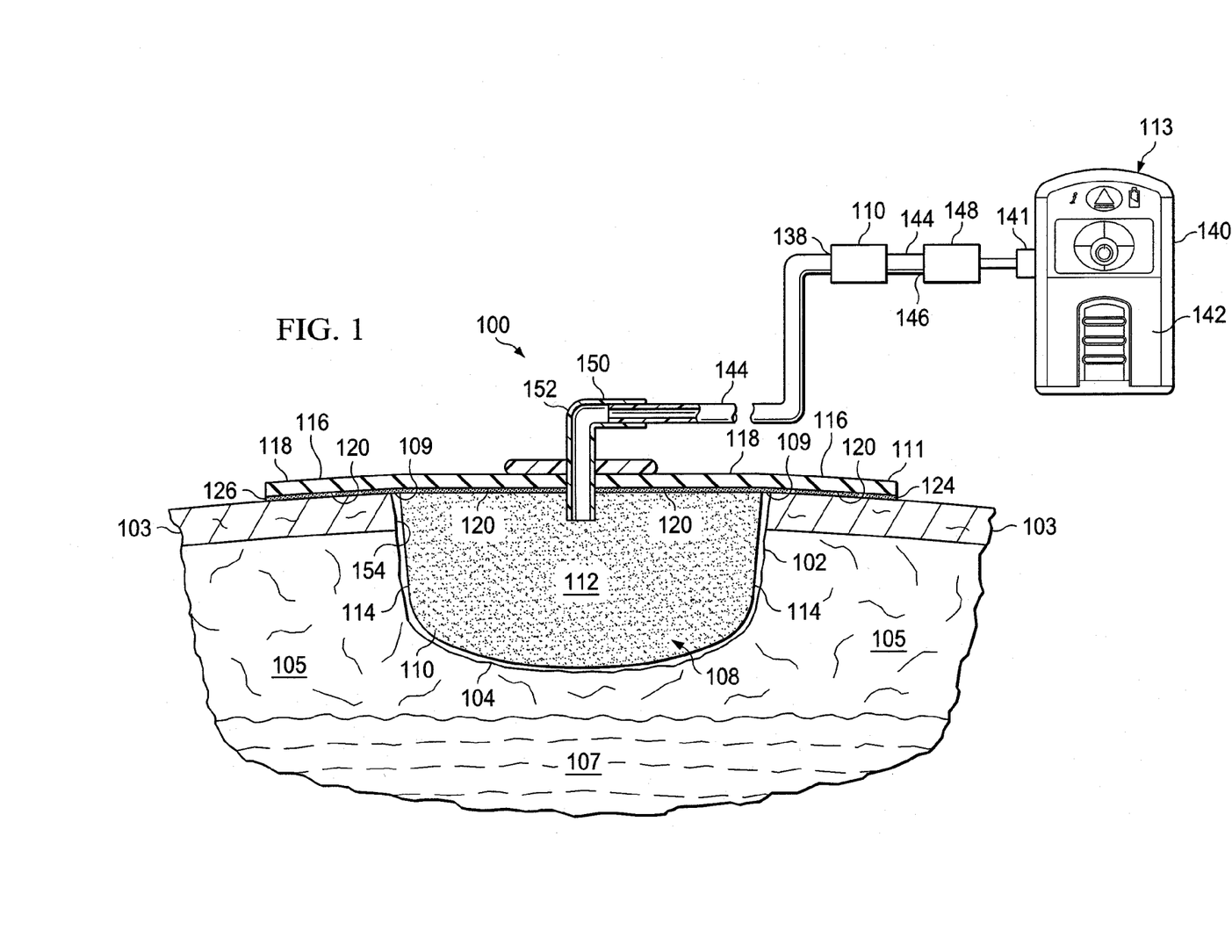
FIG. 1 is a schematic diagram with a portion shown in cross section of an illustrative, non-limiting embodiment of a dynamic, reduced-pressure treatment system.

Referring now primarily to FIG. 1, an illustrative embodiment of a dynamic, reduced-pressure treatment system 100 for treating a tissue site 104, e.g., a wound 102, a damaged area of tissue, is presented. The wound 102 may involve epidermis 103, dermis 105, and subcutaneous tissue 107. The dynamic, reduced-pressure treatment system 100 may also be used at other tissue sites. The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. The dynamic, reduced-pressure treatment system 100 may include a manifold 112, an sealing member 111, a reduced-pressure delivery member 144, a reduced-pressure subsystem 113, and a wave generator 110.

The manifold 112 distributes reduced pressure and may be formed from any manifold material suitable for distributing reduced pressure. In one illustrative embodiment, the manifold 112 is made from a porous and permeable foam material and, more particularly, a reticulated, open-cell polyurethane or polyether foam that allows good permeability of wound fluids while under a reduced pressure. One such foam material that has been used is the VAC GranuFoam® Dressing available from Kinetic Concepts, Inc. (KCI) of San Antonio, Tex. Any material or combination of materials may be used for the manifold material provided that the manifold material is operable to distribute the reduced pressure. Unless otherwise indicated, as used herein, "or" does not require mutual exclusivity.

The term "manifold" as used herein generally refers to a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include, or cure to include, flow channels. The manifold material may also be a combination or layering of materials. For example, a first manifold layer of hydrophilic foam may be disposed adjacent to a second manifold layer of hydrophobic foam to form the manifold 112.

The reticulated pores of the GranuFoam® material are helpful in carrying out the manifold function, but again other materials may be used. A material with a higher or lower density (smaller pore size) than GranuFoam® material may be desirable in some situations. Among the many possible materials, the following may be used: GranuFoam® material or a Foamex® technical foam (www.foamex.com). In some instances it may be desirable to add ionic silver to the foam in a microbonding process or to add other substances to the material, such as antimicrobial agents. The manifold 112 may be a bio-absorbable material or an anisotropic material.

The sealing member 111 covers the manifold 112 and extends past a peripheral edge 114 of the manifold 112 to form an extension 116 on an intact portion of the epidermis 103. The extension 116 has a first side 118 and a second, patient-facing side 120. The extension 116 may form a fluid seal against the epidermis 103 or against a gasket (e.g., another drape portion near wound edge 109) by a sealing apparatus 124, and any references to forming a seal with the epidermis 103 should be regarded as also including a seal formed against such a gasket. The sealing apparatus 124 may take numerous forms, such as an adhesive sealing tape, or drape tape or strip; a double-side drape tape; an adhesive 126; a paste; a hydrocolloid; a hydrogel; or other sealing device. If a tape is used, the tape may be formed of the same material as the sealing member 111 with a pre-applied, pressure-sensitive adhesive. The adhesive 126 may be applied on a second, patient-facing side 120 of the extension 116. The adhesive 126 provides a fluid seal between the sealing member 111 and the epidermis 103. "Fluid seal," or "seal," means a seal adequate to maintain reduced pressure at a desired site given the particular reduced-pressure source or subsystem involved.

The sealing member 111 may be an elastomeric material. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, other non-limiting examples of sealing member materials may include a silicone drape material, such as a 3M Tegaderm® drape material, an acrylic drape material, such as one available from Avery Dennison, or an incise drape material.

The reduced-pressure subsystem 113 includes a reduced-pressure source 140, which can take many different forms, and may include the reduced-pressure interface 150 or other components to provide reduced pressure to the manifold 112. The reduced-pressure source 140 provides reduced pressure as a part of the dynamic, reduced-pressure treatment system 100. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site 104. Unless otherwise indicated, values of pressure stated herein are gauge pressures.

The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced-pressure source 140 provides reduced pressure. The reduced-pressure source 140 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically between −100 mm Hg and −300 mm Hg.

In the illustrative embodiment of FIG. 1, the reduced-pressure source 140 is shown having a reservoir region 142, or canister region. An interposed membrane filter, such as a hydrophobic or an oleophobic filter, may be interspersed between reduced-pressure delivery member 144 and the reduced-pressure source 140. A first portion 146 of reduced-pressure delivery member 144 may have one or more devices, such as device 148. For example, the device 148 may be another fluid reservoir, or collection member to hold exudates and other fluids removed. Other examples of the device 148 that may be included on the portion 146 of reduced-pressure delivery member 144 or otherwise fluidly coupled to the reduced-pressure delivery member 148 include the following non-limiting examples: a pressure-feedback device, a volume detection system, a blood detection system, an infection detection system, a flow monitoring system, a temperature monitoring system, etc. Some of these devices may be formed integrally with the reduced-pressure source 140. For example, a reduced-pressure port 141 on reduced-pressure source 140 may include a filter member that includes one or more filters, e.g., an odor filter.

The reduced pressure developed by reduce-pressured subsystem 113 is delivered through the reduced-pressure delivery member 144 to a reduced-pressure interface 150, which may be an elbow port 152. In one illustrative embodiment, the elbow port 152 is a TRAC® pad available from Kinetic Concepts, Inc. of San Antonio, Tex. The reduced-pressure interface 150 allows the reduced pressure to be delivered through the sealing member 111 to the manifold 112, as well as to a sealed space 154 in which the manifold 112 is located. The sealed space 154 is formed by the sealing member 111 over the tissue site 104. In this illustrative embodiment, the reduced-pressure interface 150 extends through the sealing member 111 and into the manifold 112. Reduced pressure is supplied by the reduced-pressure delivery member 144 to the manifold 112. The supply of reduced pressure may be direct or in conjunction with reduced-pressure interface 150.

The wave generator 110 is typically associated with the reduced-pressure delivery member 144. For example, the wave generator 110 may be fluidly coupled to the reduced-pressure delivery member 144 on a second portion 138 or with a tributary conduit (see, e.g., tributary conduit 302 in FIG. 3). The wave generator 110 imposes a wave form on the reduced pressure supplied by the reduced-pressure subsystem 113; that is, the wave generator 110 develops a wave. The wave typically causes the pressure to vary at the tissue site 104. Preferably, the wave generator 110 allows for a wide frequency range with respect to the absolute value of the pressure experienced at the tissue site 104. The frequency range of the wave may be about 0.5 Hz to about 20 Hz and greater. The wave generator 110 may also control the amplitude of the wave. The wave generator 110 may take many forms, such a piezoelectric transducer, a diaphragm member, a valve arrangement, etc.

The wave generator 110 creates a wave, or change in the pressure or energy in the reduced pressure in the reduced-pressure delivery member 144. The change could be accomplished with a sonic wave or a pressure wave, and so the term "wave generator" has been used. The wave generator 110 may function to develop a sonic wave or a pressure wave by electrical means or mechanical means. The wave generator 110 may utilize a reduced-pressure source, gear set using kinetic motion, piezoelectric transducer, a diaphragm member, a valve arrangement, etc. With respect to mechanical options, anything that produces a mechanical variation may be used, such as a displacement device. The wave generator 110 may also be an electrically-powered membrane. Other non-limiting examples of devices and arrangements that may be used as the wave generator 110 will be presented further below in connection with FIGS. 2-4.

In operation, according to one illustrative embodiment, of the dynamic, reduced-pressure treatment system 100, the manifold 112 is placed adjacent to the tissue site 104, and the sealing member 111 is placed over the tissue site 104, manifold 112, and a portion of the epidermis 103 to form a fluid seal. The fluid seal creates the sealed space 154. If not already installed, the reduced-pressure interface 150 is fluidly coupled to the sealed space 154. The reduced-pressure delivery member 144 is fluidly coupled to the reduced-pressure source 140 and the reduced-pressure interface 150. In this embodiment, the wave generator 110 is associated with the reduced-pressure delivery member 144. When the reduced-pressure source 140 is activated, reduced pressure may be provided to the manifold 112 and ultimately to tissue site 104, and when the wave generator 110 is activated, the wave generator 110 imparts a wave and provides dynamic pressure or energy variation at the wound site 104.

As previously noted, the wave generator 110 may take many forms, such as a piezoelectric transducer, a diaphragm member, or an arrangement of valves, such as solenoid-operated valves. A number of different, non-limiting, illustrative embodiments of wave generators will now be presented.

Figure 2:
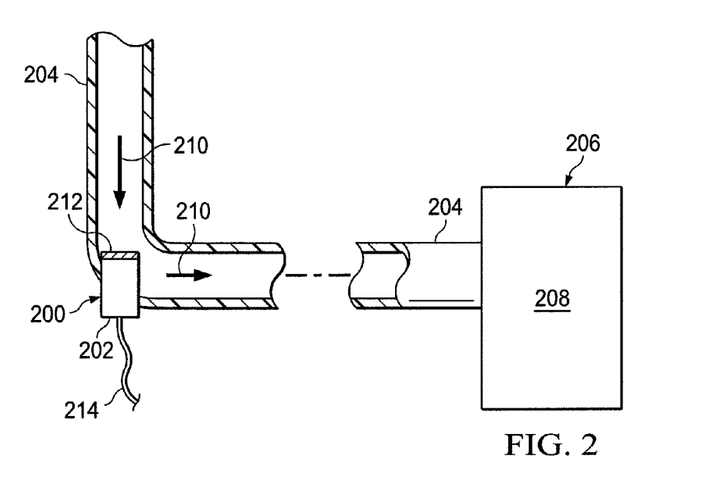
FIG. 2 is a schematic diagram with a portion shown in cross section of an illustrative, non-limiting embodiment of a wave generator for use with an embodiment of a dynamic, reduced-pressure treatment system.

Referring now primarily to FIG. 2, an illustrative embodiment of a wave generator 200 for use as part of a dynamic, reduced-pressure treatment system is presented. For example, the wave generator 200 may be used as the wave generator 110 in the dynamic, reduced-pressure treatment system of FIG. 1. In forming the wave generator 200, a piezoelectric transducer 202 is fluidly coupled, i.e., is placed in fluid communication with, a reduced-pressure delivery member 204. The reduced-pressure delivery member 204 receives reduced pressure from a reduced pressure subsystem 206, which includes a reduced-pressure source 208. The reduced-pressure subsystem 206 introduces reduced pressure into the reduced-pressure delivery member 204. The reduced-pressure subsystem 206 also receives fluids through the reduced-pressure delivery member 204 as suggested by arrows 210. In this illustrative embodiment, the wave generator 200 has been fluidly coupled to the reduced-pressure delivery member 204.

The wave generator 200 has a movable face member 212 that extends into an interior portion of the reduced-pressure delivery member 204 or is otherwise fluidly coupled to fluid within the reduced-pressure delivery member 204. The movable face member 212 moves relative to the reduced-pressure delivery member 204 at a frequency that may be controlled by a power-and-control connection 214. The power-and-control connection 214 may be a separate power cord and a device for setting and controlling the frequency of the movable face member 212 or the amplitude of the movement of the movable face member 212. The movable face member 212 imparts a wave onto the fluid already present in reduced-pressure delivery member 204. The wave causes the absolute pressure or energy delivered to vary with a frequency in the range of 0.5 Hz to 20 Hz or greater.

In still a more particular illustrative, non-limiting embodiment, the wave generator 200 may be a piezoelectric transducer with a piezoelectric member comprising the movable face member 212. In this embodiment, the movable face member 212 is electrically driven. In response to receiving a desired wave form or frequency information, the wave generator 200 may develop a wave form in the fluid of the reduced-pressure delivery member 204 with the desired frequency or wave form using physical displacement of the movable face member 212. The possible frequency range, or spectrum, for the wave developed within the reduced-pressure delivery member 204 with this approach is large from 0.5 Hertz to 20 Hertz and higher. The frequency may include any subset of the previously stated range, e.g., 5-20 Hz, 10-20 Hz, 5-15 Hz, etc.

Again, the wave generator may take numerous other forms. The wave generator may be a mechanically or electrically activated wave generator or the wave generator may utilize a diaphragm or may utilize a system of valves that turn on and off to achieve the desired effect. A device could be added to the reduced-pressure delivery conduit to press and close, i.e., pinch, the conduit or delivery member, e.g., the reduced-pressure delivery member 144 in FIG. 1, in a pattern that causes a pressure wave. Another illustrative, non-limiting embodiment follows.

Figure 3:
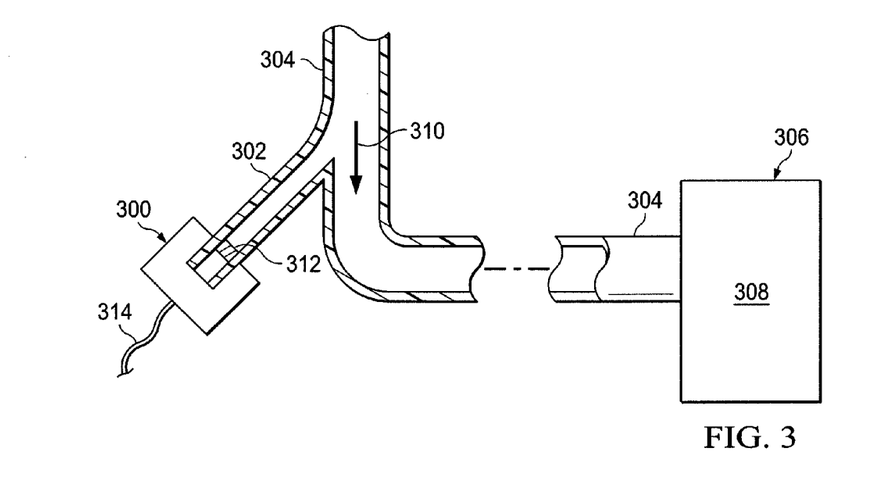
FIG. 3 is a schematic diagram with a portion shown in cross section of another illustrative, non-limiting embodiment of a wave generator for use with an embodiment of a dynamic, reduced-pressure treatment system.

Referring now primarily to FIG. 3, another illustrative embodiment of a wave generator 300 is presented. The wave generator 300 includes a tributary conduit (or lumen) 302 that is fluidly coupled to a reduced-pressure delivery member 304. The reduced-pressure delivery member 304 is fluidly coupled to a reduced-pressure subsystem 306. The reduced-pressure subsystem 306 includes a reduced-pressure source 308. The reduced-pressure subsystem 306 delivers reduced pressure to the reduced-pressure delivery member 304. At the same time, the reduced-pressure subsystem 306 pulls and receives fluid as suggested by arrow 310.

The wave generator 300 includes a wave-imparting member 312, which may be a diaphragm pump, a piston, a piezoelectric member, or any device that is operable to produce a pressure or energy wave on the fluid within the reduced-pressure delivery member 304. One or more power-and-control connection members 314 may be coupled to the wave generator 300 to provide electrical power and to control the amplitude or frequency of the energy or pressure wave imparted.

Figure 4:
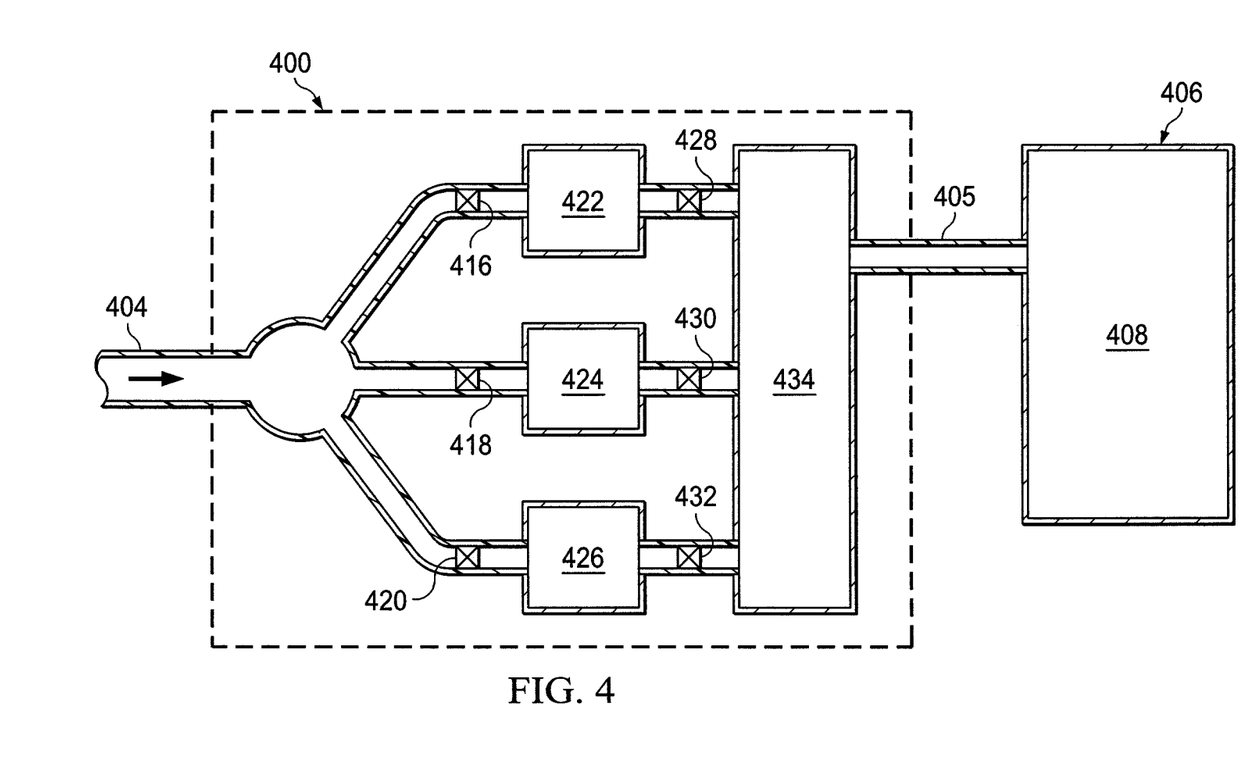
FIG. 4 is a schematic diagram of another illustrative embodiment of a wave generator for use with an embodiment of a dynamic, reduced-pressure treatment system.

Referring now primarily to FIG. 4, another illustrative embodiment of a wave generator 400 is presented. The wave generator 400 is fluidly coupled to a reduced-pressure delivery member 404. The wave generator 400 includes a plurality of valves, e.g., a first valve 416, a second valve 418, and a third valve 420. The wave generator 400 may further include a plurality of chambers, e.g., a first chamber 422, second chamber 424, and third chamber 426. A plurality of regulators, e.g., a first regulator 428, a second regulator 430, and a third regulator 432, is associated with the plurality of chambers. The first pressure regulator 428 is fluidly coupled to the first chamber 422. The second pressure regulator 430 is fluidly coupled to the second chamber 424. Similarly, the third pressure regulator 432 is fluidly coupled to the third chamber 426. Each pressure regulator 428, 430, 432 is operable to regulate pressure, e.g., operable to step down the pressure to a desired level.

A manifold chamber 434 is fluidly coupled to the pressure regulators 428, 430, 432 and provides reduced pressure thereto. The reduced pressure is supplied by a reduced-pressure subsystem 406 through a reduced-pressure supply conduit 405 to the manifold chamber 434. The reduced-pressure subsystem 406 may include a reduced-pressure source 408. The pressure can be controlled in each of the chambers 422, 424, and 426 to establish the desired pressure level. In this regard, the pressure regulators 428, 430, and 432 may reduce or increase the pressure as needed. Typically, the pressure regulators, e.g., regulators 428, 430, and 432, increase the absolute value of the pressure in the chambers, e.g., chambers 422, 424, and 426.

As a non-limiting example, the pressure in the first chamber 422 may be $P_1$, the pressure in the second chamber 424 may be $P_2$, the pressure in the third chamber 426 may be $P_3$, and $P_1 > P_2 > P_3$. Thus, opening and closing of the valves 416, 418, 420 may be sequenced to expose the fluid in reduced-pressure delivery member 404 to different pressures ($P_1$, $P_2$, and $P_3$), and thereby creates a wave. A controller may be associated with the valves 416, 418, 420, which may be solenoid valves, to coordinate the opening and closing of the valves 416, 418, 420. The opening and closing of the valves 416, 418, and 420 may allow for a wave to be generated with a frequency in the range of 0.5 Hz to 20 Hz and greater. The frequency range may be any subset of the previously stated range.

The dynamic variation of pressure or energy by the wave generator, e.g., 110, 200, 300, 400 at the tissue site, e.g., tissue site 104, may help with the healing process. The wave generator may help to debride or clean the wound in a continuous fashion. The wave generator may generally help keep the wound cleaner by removing dead tissue. In addition, the wave generator may de-sensitize nerves and thereby help reduce the patient's pain. The wave generator may also help provide a dynamic motion to the tissue that causes tissue to form with a certain orientation.

The wave generator, e.g., wave generator 110, 200, 300, 400, may be located at various locations. Depending on how rigid aspects of the dynamic, reduced-pressure treatment system are, the wave generator may need to be close to the tissue site or may be positioned further from the tissue site. Thus, if the maximum amplitude of the wave generator is not adequate for a given location, the wave generator may need to be moved closer, and if the maximum amplitude of the wave generator is more than adequate, the wave generator could be positioned further away from the tissue site. The compressibility of the fluid in the reduced-pressure delivery member will also be a factor in determining the position of the wave generator with respect to the tissue site.

It should be appreciated that the more incompressible the fluid in the reduced-pressure delivery member, e.g., the delivery member 144 in FIG. 1, is, the less energy that is required to deliver a certain amplitude for a wave or alternatively the further the wave generator 110 may be located from the tissue site 104 without expending any additional energy. To help make the fluid more incompressible for purposes of transmitting amplitude or for other reasons, the reduced-pressure delivery member 144 may be formed in such a way as to provide a segregated portion for the liquid and another portion for any gases. By segregating the fluid from any gases, a substantially incompressible fluid or more incompressible fluid than would otherwise exist may result and be utilized with the wave generator 110. Moreover, segregating the more incompressible fluid portion may facilitate flow of fluids from the wound site 104 toward the reduced-pressure subsystem 113 with a minimal risk of blockage. The reduced-pressure delivery conduit 144 may be formed in a number of ways to achieve this desired performance, and illustrative, non-limiting embodiments are described below in connection with FIGS. 5-8.

Figure 5:
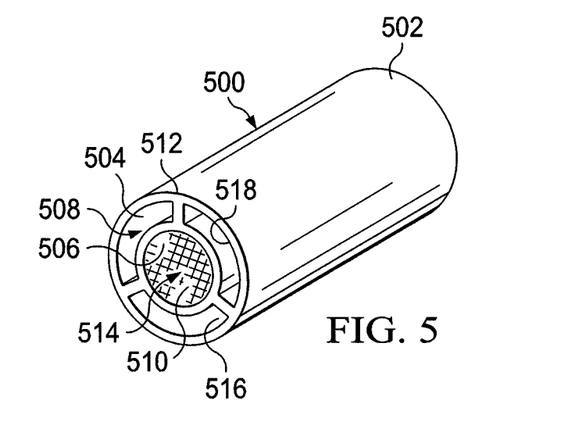
FIG. 5 is a schematic, perspective view of an illustrative embodiment of a reduced-pressure delivery member for use with an embodiment of a reduced-pressure treatment system.

Referring now primarily to FIG. 5, a reduced-pressure delivery member 500 may be formed as a conduit 502 that includes at least one lumen, e.g., first lumen 504, for transmitting a liquid (a substantially incompressible fluid), and at least one lumen, e.g., second lumen 506, for transmitting a gas. The first lumen 504 has a first interior space 508. The second lumen 506 has a second interior space 510 that is covered proximate a distal end 512 by a first liquid-impermeable-and-gas-permeable member 514. The liquid-impermeable-and-gas-permeable member 514 is operable to substantially restrict liquid while substantially allowing gas to enter. In addition to the first liquid-impermeable-and-gas-permeable member 514, which is located proximate the distal end 512, one or more additional liquid-impermeable-and-gas-permeable members 514 may be located at discrete locations on the interior of the second lumen 506 or disposed continuously throughout the second interior space 510 of the second lumen 506.

The first liquid-impermeable-and-gas-permeable member 514 may be made from any material that is liquid impermeable but gas permeable. The first liquid-impermeable-and-gas-permeable member 514 may be formed, as one non-limiting example, from a synthetic fluoropolymer such as a poly-tetrafluoroethylene material (PTFE). For the illustrative embodiment of FIG. 5, a third lumen 516 and a fourth lumen 518, which are both analogous to first lumen 504, are provided and are available to transmit a fluid. The lumens 504, 506, 516, 518 may be made of any fluid impermeable, flexible material, such as high-density polyethylene (HDPE), high impact polystyrene (HIPS), low-density polyethylene (LDPE), nylon, polycarbonate, polypropylene, polyethylene, polyvinyl chloride (PVC), urethanes, etc.

The first liquid-impermeable-and-gas-permeable member 514 substantially restricts entry into the second lumen 506 to gas while liquids may enter the first lumen 504 (and lumens 516 and 518). The liquid in the first lumen 504 (or lumens 516 and 518) may be used with a wave generator to transmit a wave or may be used to efficiently remove fluids. The wave generator, e.g., wave generator 110 in FIG. 1, may be fluidly coupled to the first interior space 508 of the first lumen 504 and may also be fluidly coupled to the third lumen 516 and the fourth lumen 518. Thus, the wave generated by the wave generator is delivered through the liquid, or incompressible fluid, in the first lumen 504 or other lumens.

Figure 6:
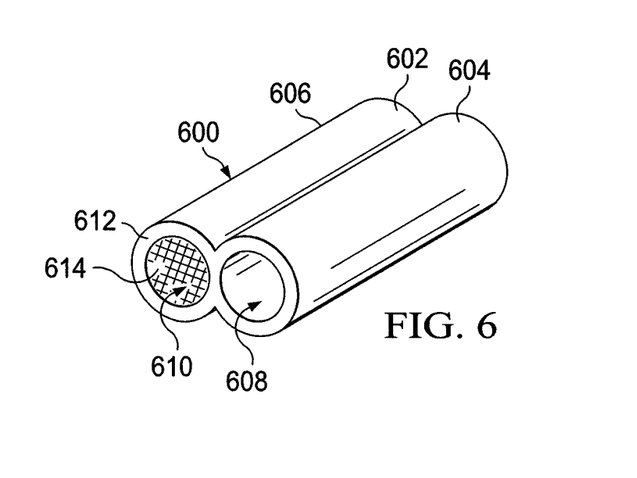
FIG. 6 is a schematic, perspective view of an illustrative, non-limiting embodiment of a reduced-pressure delivery member for use with an embodiment of a reduced-pressure treatment system.

Referring now primarily to FIG. 6, another illustrative embodiment of a reduced-pressure delivery member 600 is presented. The reduced-pressure delivery member 600 may be formed as a conduit 602 that includes at a first lumen 604 for transmitting a liquid and a second lumen 606 for transmitting gases. The first lumen 604 has a first interior space 608. The second lumen 606 has a second interior space 610 that is covered proximate a distal end 612 by a first liquid-impermeable-and-gas-permeable member 614, which is operable to substantially restrict liquid while substantially allowing gas to enter. In addition to the first liquid-impermeable-and-gas-permeable member 614, additional liquid-impermeable-and-gas-permeable members may be distributed at discrete locations or continuously throughout the second interior space 610 of the second lumen 606. The first liquid-impermeable-and-gas-permeable member 614 may be made from the same material as the first liquid-impermeable-and-gas-permeable member 514 in FIG. 5. The lumens 604 and 606 may be made of any fluid impermeable, flexible material. A wave generator, e.g., wave generator 110 in FIG. 1, may be fluidly coupled to the first lumen 604 for imparting a wave.

Figure 7:
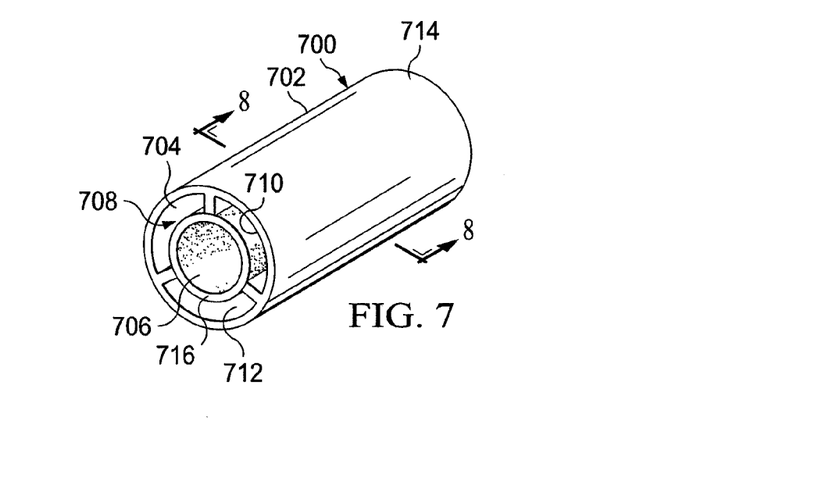
FIG. 7 is a schematic, perspective view of an illustrative, non-limiting embodiment of a reduced-pressure delivery member for use with an embodiment of a reduced-pressure treatment system.
Figure 8:
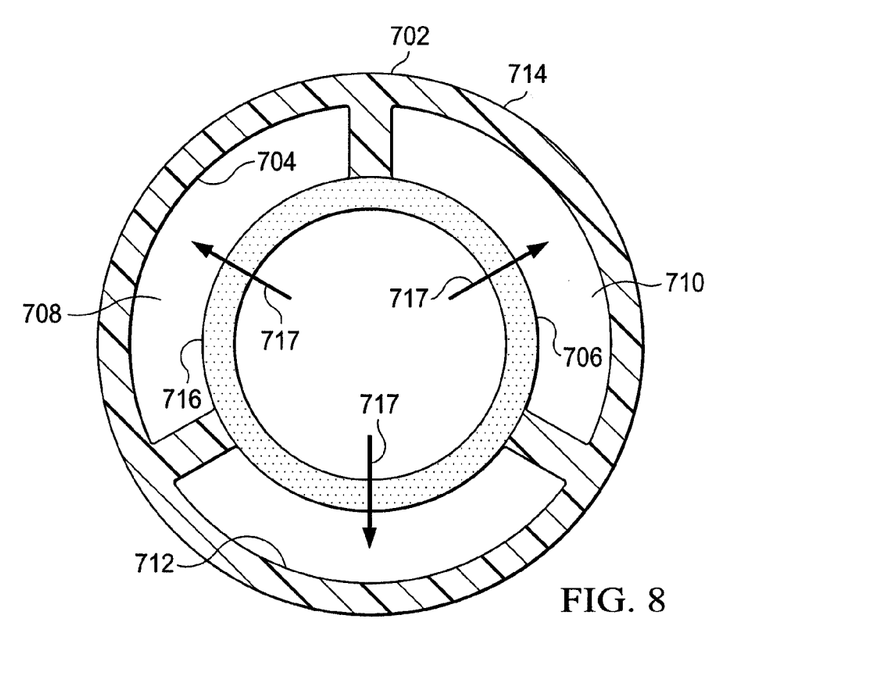
FIG. 8 is a schematic cross section of the reduced-pressure delivery member of FIG. 7 taken along line 8-8.

Referring now primarily to FIG. 7, another illustrative embodiment of a reduced-pressure delivery member 700 is presented. The reduced-pressure delivery member 700 may be formed as a conduit 702 that includes a first lumen 704 for transmitting gases (substantially compressible fluid), e.g., air, and a second lumen 706 for transmitting a liquid (substantially incompressible fluid). The first lumen 704 has a first interior space 708. In this illustrative embodiment, a third lumen 710 and a fourth lumen 712 are provided for transmitting a gas.

The first lumen 704, third lumen 710, and fourth lumen 712 are spaced and concentrically disposed about the second lumen 706. The second lumen 706 is disposed within an interior space of the other lumens 704, 710, 712 and defines an interior conduit therein. An exterior wall 714 of the conduit 702, which makes up the exterior walls of the first lumen 704, third lumen 710, and fourth lumen 712, is made from a fluid impermeable, flexible material, such as the materials previously mentioned. The exterior wall 716 of the second lumen 706 is made from a liquid-impermeable-gas-permeable material, such as a synthetic fluoropolymer, e.g., a poly-tetrafluoroethylene material (PTFE). The exterior wall 716 of the second lumen 706 is also an interior wall of the first lumen 704, third lumen 710, and fourth lumen 712. In one alternative, illustrative embodiment, the first lumen 704 may be a 360 degree conduit with a first interior space into which the second lumen 706 is inserted.

As fluid is pulled through the second lumen 706 of the reduced-pressure delivery member 700, gases are free to pass through the exterior wall 716 of the second lumen 706 as suggested by arrows 717 and into the first lumen 704, third lumen 710, or fourth lumen 712. As such, the fluid remaining within the second lumen 706 contains less gas and is therefore more incompressible. As previously noted, a wave generator may more easily or efficiently impart a wave on the fluid when the fluid is more incompressible, and a wave generator, e.g., wave generator 110 in FIG. 1, may be fluidly coupled to the first lumen 704 or lumens 710 and 712 for imparting a wave thereto.

The systems and methods herein may allow reduced-pressure treatment of a wound site with dynamic pressure or energy that preferably allows high frequency variation and controls the pressure or energy wave amplitude. Moreover, it does so with reliability and with minimal energy requirements.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

The invention claimed is:

1. A dynamic, reduced-pressure treatment system for treating a tissue site on a patient, the system comprising:
   a manifold adapted to be positioned adjacent the tissue site for distributing reduced pressure to the tissue site;
   a sealing member adapted to be coupled to an epidermis of the patient to cover the manifold and to form a fluid seal between the sealing member and the tissue site;
   a reduced-pressure source for producing the reduced pressure;
   a reduced-pressure delivery member for delivering the reduced pressure from the reduced-pressure source to the manifold, the reduced-pressure delivery member adapted to transmit liquid and gas from the tissue site;
   a   liquid-impermeable-and-gas-permeable   member adapted to substantially segregate the liquid into a separate liquid flow and the gas into a separate gas flow; and
   a wave generator in fluid communication with the separate liquid flow, wherein the wave generator imparts a wave to the liquid.

2. The dynamic, reduced-pressure treatment system of claim 1, wherein the wave generator is coupled to the reduced-pressure delivery member in fluid communication between the reduced-pressure source and the sealing member.

3. The dynamic, reduced-pressure treatment system of claim 1, wherein the wave generator is operable to impart a wave to the liquid with a frequency greater than about one Hertz.

4. The dynamic, reduced-pressure treatment system of claim 1, wherein the wave generator imparts a wave to the liquid with a frequency in the range of about 0.5 Hz to about 20 Hz.

5. The dynamic, reduced-pressure treatment system of claim 1, wherein the wave generator imparts a wave to the liquid with a frequency greater than about 20 Hertz.

6. The dynamic, reduced-pressure treatment system of claim 1, wherein the wave generator comprises a piezoelectric transducer in fluid communication with the reduced-pressure delivery member.

7. The dynamic, reduced-pressure treatment system of claim wherein the wave generator comprises a diaphragm member in fluid communication with the reduced-pressure delivery member.

8. The dynamic, reduced-pressure treatment system of claim 1, wherein the wave generator comprises a plurality of chambers with valves and wherein each of the chambers is selectively in fluid communication with the reduced-pressure delivery member.

9. The dynamic, reduced-pressure treatment system of claim 1, wherein the reduced-pressure delivery member comprises a conduit, and wherein the conduit comprises:
   a first lumen for transmitting the liquid, the first lumen having a first interior space;
   a second lumen for transmitting the gas, the second lumen having a second interior space; and
   wherein the liquid-impermeable-and-gas-permeable member is coupled to the second lumen in at least a portion of the second interior space.

10. The dynamic, reduced-pressure treatment system of claim 1, wherein the reduced-pressure delivery member comprises a conduit, and wherein the conduit comprises:
   a first lumen for transmitting the liquid, the first lumen having a first interior space;
   a second lumen for transmitting the gas, the second lumen having a second interior space;
   wherein the liquid-impermeable-and-gas-permeable member is coupled to the second lumen in at least a portion of the second interior space; and
   wherein the wave generator is in fluid communication with the first lumen.

11. The dynamic, reduced-pressure treatment system of claim 1, wherein the reduced-pressure delivery member comprises a conduit, and wherein the conduit comprises:
   a first lumen for transmitting the liquid, the first lumen having a first interior space;
   a second lumen for transmitting the gas, the second lumen having a second interior space;
   wherein the liquid-impermeable-and-gas-permeable member is coupled to the second lumen in at least a portion of the second interior space; and
   wherein the liquid-impermeable-and-gas-permeable member comprises a synthetic fluoropolymer.

12. The dynamic, reduced-pressure treatment system of claim 1, wherein the reduced-pressure delivery member comprises a conduit, and wherein the conduit comprises:
   a first lumen for transmitting the liquid, the first lumen having a first interior space;
   a second lumen for transmitting the gas, the second lumen having a second interior space;
   wherein the liquid-impermeable-and-gas-permeable member is coupled to the second lumen in at least a portion of the second interior space;
   wherein the liquid-impermeable-and-gas-permeable member comprises a synthetic fluoropolymer; and
   wherein the synthetic fluoropolymer comprises a polytetrafluoroethylene material (PTFE).

13. The dynamic, reduced-pressure treatment system of claim 1, wherein the reduced-pressure delivery member comprises:
   a first lumen for transmitting the gas, the first lumen having a first interior space;
   a second lumen for transmitting the liquid, the second lumen having a second interior space;
   the first lumen comprising a fluid impermeable material; and
   the second lumen formed from the liquid-impermeable-and-gas-permeable member and disposed within the first interior space.

14. The dynamic, reduced-pressure treatment system of claim 1, wherein the reduced-pressure delivery member comprises:
   an outer lumen having a first interior space and formed from a fluid impermeable material and wherein the first interior space comprises a liquid flow path;
   an inner flow member comprising a lumen formed from the liquid-impermeable-and-gas-permeable member and disposed within the first interior space; and
   wherein the wave generator is in fluid communication with the liquid flow path.

15. The dynamic, reduced-pressure treatment system of claim 1, wherein the reduced-pressure delivery member comprises:
   an outer lumen having a first interior space and formed from a fluid impermeable material and wherein the first interior space comprises a liquid flow path;
   an inner flow member comprising a lumen formed from the liquid-impermeable-and-gas-permeable member and disposed within the first interior space;
   wherein the wave generator is in fluid communication with the liquid flow path; and
   wherein the liquid-impermeable-and-gas-permeable member comprises a synthetic fluoropolymer.

16. The dynamic, reduced-pressure treatment system of claim 1, wherein the reduced-pressure delivery member comprises:
   an outer lumen having a first interior space and formed from a fluid impermeable material and wherein the first interior space comprises a liquid flow path;
   an inner flow member comprising a lumen formed from the liquid-impermeable-and-gas-permeable member and disposed within the first interior space;
   wherein the wave generator is in fluid communication with the liquid flow path;
   wherein the liquid-impermeable-and-gas-permeable member comprises a synthetic fluoropolymer; and
   wherein the synthetic fluoropolymer comprises a polytetrafluoroethylene material (PTFE).

17. A method of manufacturing a dynamic, reduced-pressure treatment system for treating a tissue site on a patient, the method comprising the steps of:

providing a manifold for placing adjacent to the tissue site and operable to distribute reduced pressure to the tissue site;

providing a sealing member for coupling to an epidermis of the patient and operable to cover the manifold and to form a fluid seal between the sealing member and the tissue site;

providing a reduced-pressure source for developing a reduced pressure;

providing a reduced-pressure delivery member for delivering reduced pressure from the reduced-pressure source to the manifold, the reduced-pressure delivery member comprising a first lumen and a second lumen;

segregating the first lumen from the second lumen with a liquid-impermeable-and-gas-permeable member, the liquid-impermeable-and-gas-permeable member adapted to substantially preclude liquid from entering the second lumen to provide a liquid flow in the first lumen and a gas flow in the second lumen; and coupling a wave generator in fluid communication with the first lumen, the wave generator for imparting a wave to the liquid flow in the first lumen.

18. A method for treating a tissue site on a patient, the method comprising the steps of:

disposing a manifold adjacent to the tissue site, wherein the manifold is operable to distribute reduced pressure to the tissue site;

placing a sealing member on an epidermis of the patient to cover the manifold and to form a fluid seal between the sealing member and the tissue site;

fluidly coupling a reduced-pressure delivery member to the manifold;

fluidly coupling the reduced-pressure delivery member to a reduced-pressure source;

providing reduced pressure to the manifold from the reduced-pressure source;

substantially segregating liquid and gas carried by the reduced pressure and transmitted through the reduced-pressure delivery member from the tissue site into a separate liquid flow and a separate gas flow in the reduced pressure delivery member; and coupling a wave generator in fluid communication with the separate liquid flow for imparting a wave to the liquid flow.

19. The method of claim 18, wherein the step of coupling a wave generator comprises fluidly coupling the wave generator to the reduced-pressure delivery member between the reduced-pressure source and the sealing member.

20. The method of claim 18, wherein the wave generator imparts a wave to the liquid flow with a frequency greater than about one Hertz.

21. The method of claim 18, wherein the wave generator imparts a wave to the liquid flow with a frequency in the range of about 0.5 to about 20 Hertz.

22. The method of claim 18, wherein the wave generator imparts a wave to the liquid flow with a frequency greater than about 20 Hertz.

23. The method of claim 18, wherein the wave generator comprises a piezoelectric transducer in fluid communication with the reduced-pressure delivery member.

24. The method of claim 18, wherein the wave generator comprises a diaphragm member in fluid communication with the reduced-pressure delivery member.

25. The method of claim 18, wherein the wave generator comprises a plurality of chambers with valves and wherein each of the chambers selectively in fluid communication with the reduced-pressure delivery member.

* * * * *